United States Patent [19]

Martin et al.

[11] Patent Number: 5,134,360
[45] Date of Patent: Jul. 28, 1992

[54] APPARATUS AND METHOD FOR CRITICAL CURRENT MEASUREMENTS

[75] Inventors: Joe A. Martin, Espanola; Robert C. Dye, Los Alamos, both of N. Mex.

[73] Assignee: The United States of America as represented by the United States Department of Energy, Washington, D.C.

[21] Appl. No.: 670,111

[22] Filed: Mar. 15, 1991

[51] Int. Cl.⁵ .............................................. G01N 27/00
[52] U.S. Cl. .................................. 324/71.6; 324/654; 324/655; 324/248; 505/843
[58] Field of Search ...................... 324/654, 71.6, 655, 324/248; 505/843

[56] References Cited

U.S. PATENT DOCUMENTS

| | | | |
|---|---|---|---|
| 4,851,762 | 7/1989 | Kim et al. | 324/71.6 |
| 4,904,929 | 2/1990 | Bohandy et al. | 324/71.6 |
| 5,015,952 | 5/1991 | Doss | 324/654 X |
| 5,039,944 | 8/1991 | Kim et al. | 324/248 X |
| 5,059,891 | 10/1991 | Bohandy et al. | 324/71.6 |
| 5,065,087 | 11/1991 | Kita et al. | 324/71.6 |

*Primary Examiner*—Kenneth A. Wieder
*Assistant Examiner*—Glenn W. Brown
*Attorney, Agent, or Firm*—Bruce H. Cottrell; Paul D. Gaetjens; William R. Moser

[57] ABSTRACT

An apparatus for the measurement of the critical current of a superconductive sample, e.g., a clad superconductive sample, the apparatus including a conductive coil, a means for maintaining the coil in proximity to a superconductive sample, an electrical connection means for passing a low amplitude alternating current through the coil, a cooling means for maintaining the superconductive sample at a preselected temperature, a means for passing a current through the superconductive sample, and, a means for monitoring reactance of the coil, is disclosed, together with a process of measuring the critical current of a superconductive material, e.g., a clad superconductive material, by placing a superconductive material into the vicinity of the conductive coil of such an apparatus, cooling the superconductive material to a preselected temperature, passing a low amplitude alternating current through the coil, the alternating current capable of generating a magnetic field sufficient to penetrate, e.g., any cladding, and to induce eddy currents in the superconductive material, passing a steadily increasing current through the superconductive material, the current characterized as having a different frequency than the alternating current, and, monitoring the reactance of the coil with a phase sensitive detector as the current passed through the superconductive material is steadily increased whereby critical current of the superconductive material can be observed as the point whereat a component of impedance deviates.

18 Claims, 5 Drawing Sheets

APPARATUS AND METHOD FOR CRITICAL CURRENT MEASUREMENTS

This invention is the result of a contract with the Department of Energy (Contract No. W-7405-ENG-36).

FIELD OF THE INVENTION

The present invention relates to the measurement of critical current of superconductive materials, particularly clad superconductive materials, and more particularly metal clad high temperature ceramic superconductive materials.

BACKGROUND OF THE INVENTION

Current state of the art development of high temperature ceramic superconductors for power applications, e.g., motors, solenoids, magnetic levitation, power transmission and power storage, centers on the encapsulation or cladding of bulk powders of ceramic superconductors in conductive metal sheaths, e.g., silver, to permit rolling or drawing of the composite structure into wires or tapes. The final structures consist of long lengths of high temperature superconductor (HTS) cores surrounded by the conductive metal cladding. Current cladding processes have not generally yielded high quality HTS wires or tapes directly. The rolled or drawn wires or tapes must generally be thermally annealed after fabrication to achieve useful electrical transport properties. Achieving optimum electrical transport properties, such as high critical currents and high critical current densities, in bulk HTS materials has proven exceedingly difficult and is the present focus of worldwide research efforts. Thus, techniques that probe electrical transport properties in bulk HTS materials and especially in clad HTS materials are essential to successful development programs.

Measurement of critical electrical transport properties, e.g., critical currents ($I_c$), and subsequent calculation of critical current densities ($J_c$), in clad HTS materials presents a significant challenge because conventional measurement techniques using probes, such as a standard resistivity four point probe, require direct access or contact with the HTS material itself. Direct contact with the HTS core is impossible with a clad structure. The cladding of such a clad HTS material effectively short circuits the standard resistivity four point probe measurement and can lead to the measurement of erroneous values for the critical currents and calculation of erroneous values for critical current densities. Therefore, such conventional measurement techniques are of limited utility.

Accordingly, it is an object of this invention to provide a method for measuring critical currents in superconductor materials, especially in clad HTS materials.

It is a further object of this invention to provide a non-contact method for measuring critical currents in superconductor materials, especially in clad HTS materials.

Yet another object of this invention is to provide an apparatus for measuring critical currents in clad superconductor materials, especially in clad HTS materials.

Still another object of the invention is to provide an apparatus and method for determining the critical current densities in clad superconductor materials, especially in clad HTS materials.

SUMMARY OF THE INVENTION

To achieve the foregoing and other objects, and in accordance with the purposes of the present invention, as embodied and broadly described herein, the present invention provides an apparatus for the measurement of the critical current of a superconductive sample, e.g., a clad superconductive sample, including a conductive coil, a means for maintaining the coil in proximity to a superconductive sample, e.g., a clad superconductive sample, an electrical connection means for passing a low amplitude alternating first current through the coil, a cooling means for maintaining the superconductive sample at a preselected temperature, a means for passing a second current through the superconductive sample, and, a means for monitoring inductive reactance of the coil.

The present invention further provides a process of measuring the critical current of a superconductive material, e.g., a clad superconductive material, by placing a superconductive material, e.g., a clad superconductive material, into the vicinity of a conductive coil, the coil included in an apparatus further including a coil mount, an electrical connection means for passing a low amplitude alternating first current through the coil, a means for passing a second current through the superconductive material, and, a means for monitoring reactance of the coil, cooling the superconductive material to a preselected temperature, passing the low amplitude alternating first current through the coil, the alternating current capable of generating a magnetic field sufficient to penetrate, e.g., any cladding, and to induce eddy currents in the superconductive material, passing a steadily increasing second current through the superconductive material, the second current characterized as having a different frequency than the alternating current, and, monitoring the reactance of the coil with a phase sensitive detector as the second current is steadily increased whereby the critical current of the superconductive material can be observed as the point whereat a component of impedance deviates.

DETAILED DESCRIPTION

Figure 1:
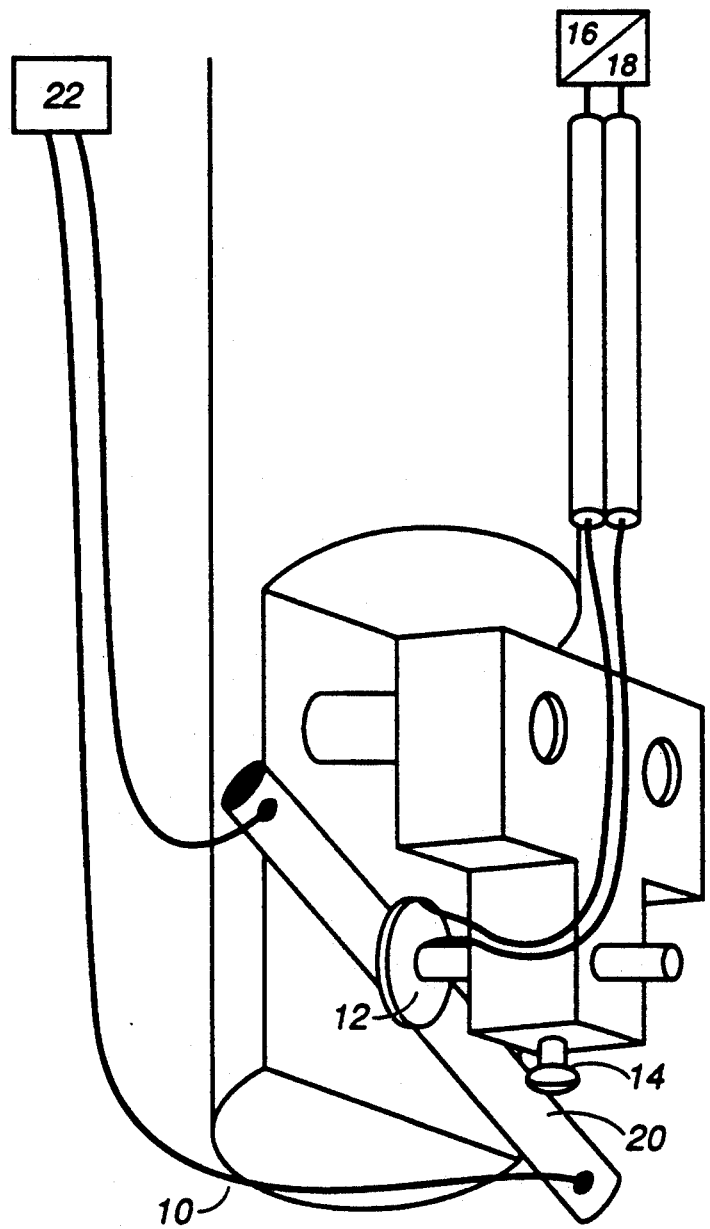
FIG. 1 shows an apparatus of the present invention.

The present invention concerns an apparatus and process for measurement of critical currents ($I_c$) and subsequent calculation of critical current densities ($J_c$) of superconductive materials, and especially the measurement of $I_c$ for clad superconductive materials, e.g., clad HTS materials and subsequent calculation of $J_c$ for such clad superconductive materials. The present apparatus and process allow for such measurements in a non-invasive, essentially non-contact manner with the superconductive material itself, whether clad or unclad. Further, the present apparatus can be used in a process for the qualitative measurement of the relative quality or quantity of the superconductive material in, e.g., a clad superconductive structure, thereby identifying better or poorer regions of, e.g., a wire or tape.

The apparatus and process are based upon the measurement of the inductive reactance, a component of impedance, of a conductive coil situated in close proximity to, e.g., the superconductive material, generally the clad superconductive material, e.g., a clad HTS material. Measurement of the inductive reactance of such a conductive coil and subsequent plot of the inductive reactance versus current passed through the superconductive material has been found to show dramatic deviation when the critical current of the superconductive material is exceeded.

The apparatus of the present invention includes a conductive coil, a means for fixedly situating the conductive coil in proximity of the superconductive sample, a means for passing a low amplitude alternating first current through the conductive coil, a cooling means for maintaining the superconductive sample at a preselected temperature, a second means for passing a current through a superconductive sample, and a means for monitoring reactance of the conductive coil whereby critical current can be measured and critical current densities can be calculated.

The term "superconductive material" refers to materials exhibiting the property of superconductivity when such materials are cooled to or below the known critical transition temperatures, i.e., the temperature whereat such materials become superconductive. Such superconductive materials can include the "low temperature" superconductor-type materials, generally metals such as, e.g., niobium-tin ($Nb_3Sn$), or the "high temperature" superconductor-type materials, generally ceramics such as, e.g., yttrium-barium-copper oxides ($Y_1Ba_2Cu_3O_x$), bismuth-containing compositions such as those commonly referred to as the 2-2-2-3 and the 2-2-1-2 compositions, or thallium-containing compositions. Typically, superconductive materials for use in power applications are clad in a conductive metal sheath. Clad superconductive materials typically include cladding of conductive metals such as silver, gold, and copper, as well as combinations of such metals and other metals such as stainless steel that may be an outer coating upon, e.g., the silver cladding that is direct contact with the superconductive, e.g., HTS, material. There may also be a outer coating of an insulating material, such as, e.g., a plastic, an enamel paint or glass, upon the outer surface of the metal cladding.

The conductive coil of the present apparatus can be a thin wire of, e.g., copper, configured in a geometry whereby the magnetic coupling between the conductive coil and the superconductive sample is maximized. Among geometries that can be used are a planar spiral arrangement, an oblong shaped coil, or a cylindrical solenoid. The wire can generally be of any thickness or diameter suitable for producing maximum inductive reactance and will generally have a diameter of from about 0.1 mils to about 10 mils. Generally, the smaller the conductive coil, the sharper the spatial resolution of the measurement. For reinforcement and protection of the conductive coil, the coil can be embedded in a polymer such as an epoxy. Besides copper, the conductive coil may also be silver or gold, although copper is generally preferred. The conductive coil may also be comprised of superconductive material and use of a superconducting conductive coil may be most preferable as such use would reduce noise and yield a higher signal to noise ratio in the measuring system of the present apparatus.

The present apparatus and process can be characterized as involving a non-invasive process and essentially a non-contact process with regards to the measurements of a superconductive material. In the apparatus, the conductive coil is generally situated in the immediate proximity of the superconductive sample, preferably as close to the superconductive sample as possible since increasing the distance between the coil and the sample will result in decreased sensitivity. Generally, the conductive coil is fixedly situated within about 5 mils of the sample, preferably in direct contact with a clad superconductive sample. The conductive coil can be fixedly situated by any suitable mechanical means such as clamping, threading or gluing. Preferably, the conductive coil is removably attached as opposed to permanently attached to a conductive coil holder by clamping or threading.

Optionally, the superconductive sample could be fixedly situated by suitable mounting or both the superconductive sample and the conductive coil could be fixedly situated in proximity to each other. Generally, for measurements on superconductive tapes or wires, a preferred process would involve fixedly situating the conductive coil and moving the length of superconductive tape or wire past the conductive coil.

The apparatus further includes a cooling means for maintaining the superconductive sample, e.g., the clad superconductive sample, at a preselected temperature. The sample is maintained at temperatures below the critical transition temperature ($T_c$) of the superconductive material or sample. It is especially critical in the present process that the temperature of the system is maintained constant to obtain proper measurements of the critical current. Such cooling means for maintaining the sample at a preselected temperature can be a reservoir containing an appropriate cryogenic liquid, i.e., a liquid boiling at temperatures lower than the $T_c$ of the superconductive material. For the presently known superconductive materials, whether of the low temperature type or the high temperature type, such temperatures are generally attained by the use of liquid nitrogen, liquid helium or liquid hydrogen. Liquid nitrogen and liquid helium are preferred as the cryogenic liquid, and liquid nitrogen is most preferred for HTS materials having critical transition temperatures above the boiling point of liquid nitrogen. The development of superconductive materials having even higher $T_c$'s is eagerly awaited, and such further development may allow for the use of other cryogenic liquids or cryogenic mixtures with even higher boiling points. The cooling may also be accomplished by, e.g., an evacuated or inert gas filled chamber with a refrigerated stage or head upon which the conductive coil and superconductive material are attached.

In one manner of practicing the present invention, the cooling reservoir can be of sufficient size to allow complete immersion of a portion of the apparatus of the invention, in particular, the superconductive sample, the conductive coil, and the means for fixedly situating the conductive coil in proximity of the superconductive sample into the cryogenic liquid. Immersing the conductive coil may also reduce noise generated by the coil, but is not considered necessary other than for simplicity due to the close proximity of the conductive coil and the superconductive material during the operation of the process of the invention.

The apparatus further includes an electrical connection means for passing an alternating current through the conductive coil. Such an alternating current is preferably a low amplitude alternating current. Generally, by "low amplitude" is meant about 1 milliampere RMS current. The low amplitude alternating current is capable of generating a magnetic field sufficient to penetrate the clad superconductive sample, e.g., the clad HTS sample, and induce low amplitude eddy currents within the superconductive material. These low amplitude eddy currents result in modifying the impedance of the nearby conductive coil primarily by modifying the reactive component of impedance. Such a means can include an alternating current oscillator attached by, e.g., electrical leads, to selected sites of the conductive coil. Preferably, the low amplitude alternating current is also a low frequency current. By "low frequency" is meant a frequency sufficiently low to permit field penetration through any cladding thereby avoiding severe attenuation due to skin effect, i.e., localization of alternating currents in surface regions of the cladding. Generally, the frequency of the alternating current can be from about 100 hertz (Hz) to about 500 kilohertz (KHz), more preferably from about 1 KHz to about 10 KHz.

The apparatus also includes a means for passing a second current through the superconductive sample. Such a means can generally be an electrical connection means including a direct current source or an alternating current source attached by, e.g., electrical leads, to selected sites of the superconductive sample, generally to opposing ends of, e.g., a clad superconductive wire or tape. Optionally, a current could be induced in the superconductive sample by use of a second conductive coil.

The current passed through the superconductive sample can be further characterized as having a different frequency than the alternating current passing through the conductive coil. Further, the current passed through the superconductive sample is preferably not of a harmonic frequency of the alternating current. In the general practice of the present invention, the current is preferably a DC current, although in applications related to, e.g., commercial power systems, an alternating current of 50 Hz or above may be desirable.

In the process of the present invention, the current, preferably direct current, passing through the superconductive sample is gradually increased until the current reaches the critical current limit of the superconductive material of the sample. At this point, the superconductive material can no longer support current flow with zero resistance. Therefore, the eddy currents previously induced by the low-amplitude, low-frequency current in the conductive coil cease to circulate in the superconductive material thereby resulting in a dramatic increase of the impedance of the conductive coil, more particularly in the inductive reactance component of the impedance. This dramatic increase of the impedance is the indicator that the critical current limit for the superconductive material has been reached.

A means for monitoring reactance of a coil can include a phase sensitive detector capable of detecting changes in the reactive component of impedance or equivalently the phase angle of the drive signal applied to the conductive coil relative to the reference phase angle of the drive oscillator. Such a phase sensitive detector can be, e.g., a lock-in amplifier.

The present apparatus can further include a means for applying a magnetic field to the superconductive sample. The magnetic field can be applied to the superconductive sample during measurement of the critical current thereby allowing for measurement of the critical current as a function of magnetic field. This measurement may be desirable, as one critical parameter in many superconductor applications is the magnitude of the magnetic field that can be applied before the superconducting properties are lost. The magnetic field can be applied by a cylindrical solenoid with the apparatus including the superconductive sample and conductive coil inserted into the center of the solenoid as the entire apparatus is cooled to the preselected temperature.

FIG. 1 shows an embodiment of an apparatus of the present invention. In FIG. 1, a measuring probe 10 includes a conductive coil 12 attached at a fixed position by screw 14. Conductive coil 12 embedded in epoxy polymer is electrically connected to an AC oscillator 16 and to lock in amplifier 18 for monitoring reactance of the coil. A superconductive sample 20 is shown near conductive coil 12 and superconductive sample 20 is electrically connected to a current source 22. Superconductive sample 20 is generally situated in a parallel planar relationship to the plane of conductive coil 12.

Figure 2:
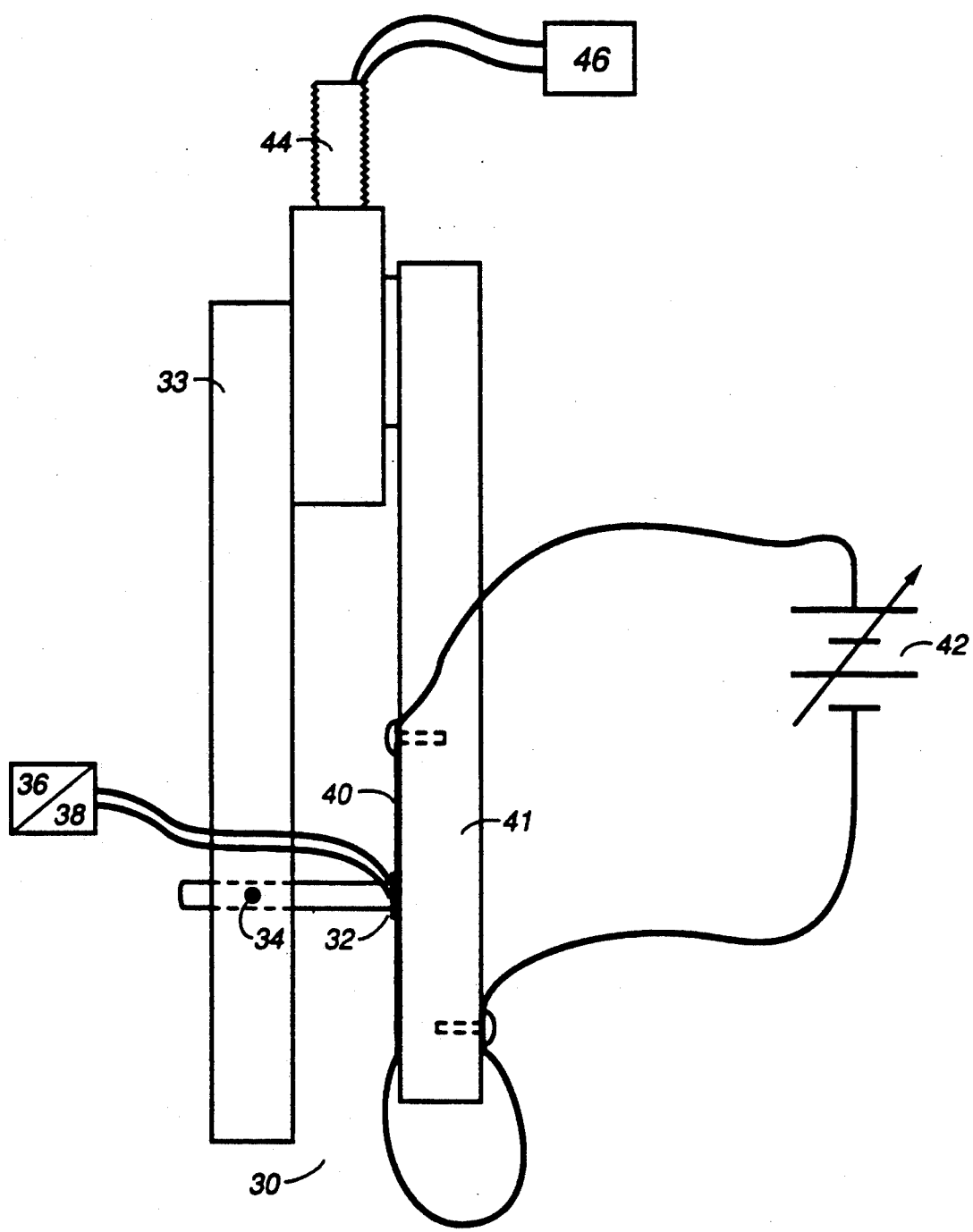
FIG. 2 shows another apparatus of the present invention.
Figure 3:
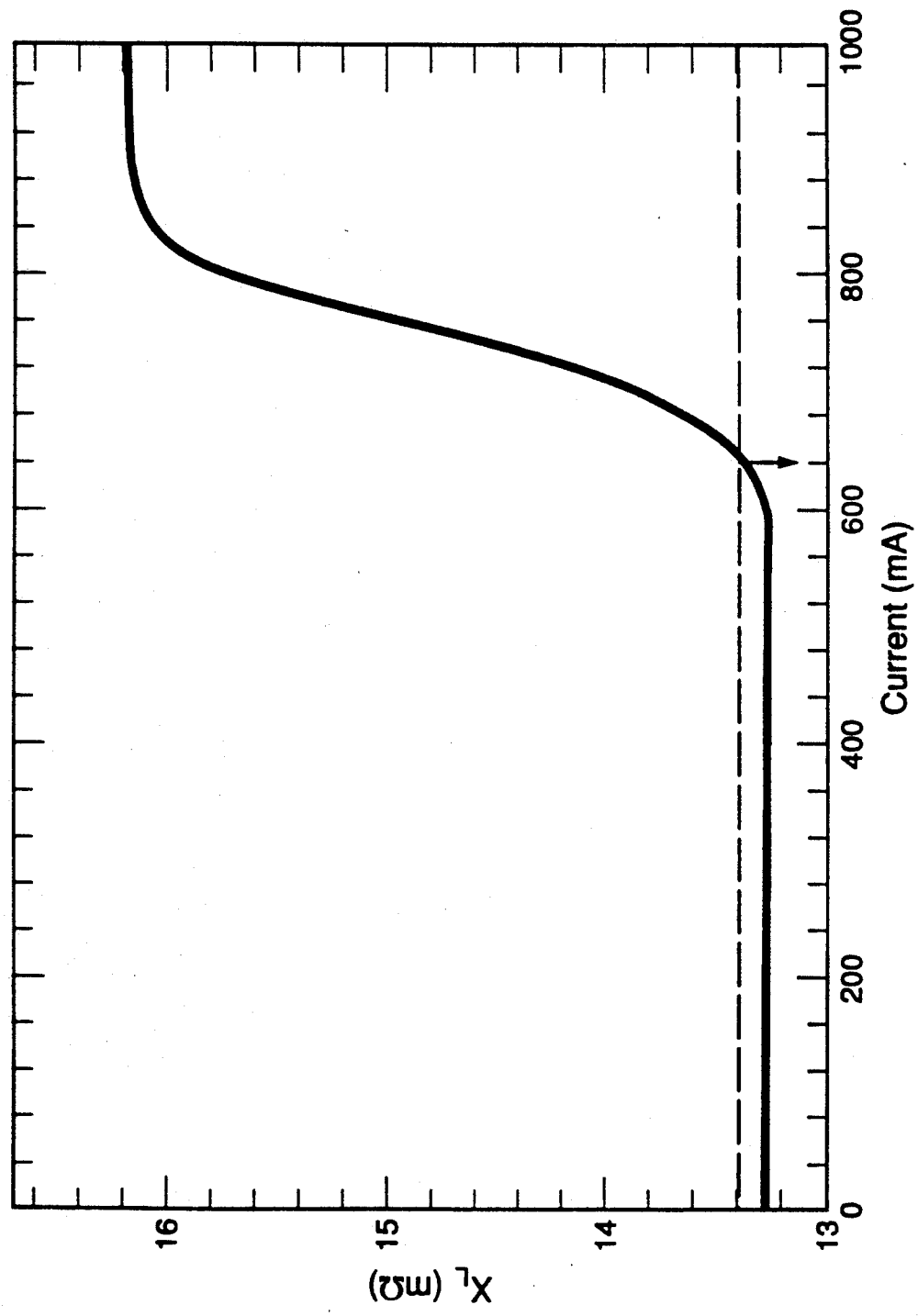
FIG. 3 shows a graph of current supplied to the clad superconductive material versus the measured inductive reactance ($X_L$) in a sample run of the present process.

FIG. 2 shows another assembly of the present invention that is useful in measuring relative critical currents across regions or lengths of a superconductive wire or tape. In FIG. 2, a measuring probe 30 includes a conductive coil 32 attached at a fixed position on fixture 33 by screw 34. Conductive coil 32 is electrically connected to an AC oscillator 36 and to lock-in amplifier 38 for monitoring reactance of the coil. A superconductive sample 40 is shown attached onto fixture 41 near conductive coil 32 and superconductive sample 40 is electrically connected to a current source 42. Fixture 41 can be moved relative to fixture 33 by drive motor 44 connected to drive motor controller 46. By moving fixture 41, superconductive sample 40 can be passed by conductive coil 32 thereby allowing for a comparative measurement of critical current along the length of superconductive sample 40. An example of such a measurement is shown in FIG. 3. Lock-in amplifier 38 and AC oscillator 36 can be separate components or can be included within a single component.

The present invention offers an opportunity to measure critical current densities along the entire length of a clad superconductive wire or tape without the need to attach numerous external leads or contact points. By passing a length of such wire or tape through the apparatus of the present invention, regions of varying $I_c$'s can be identified. For example, the present apparatus and process can be employed as an on-line monitoring system during the large scale fabrication of clad HTS wires or tapes.

The present invention is more particularly described in the following examples which are intended as illustrative only, since numerous modifications and variations will be apparent to those skilled in the art.

EXAMPLE 1

A conductive coil was formed from 40 gauge copper wire. The coil had about 80 turns in a planar, spiral type arrangement. The coil was mounted onto a probe as shown in FIG. 1 and a clad superconductive material of thallium-barium-calcium-copper oxide (a 2-2-2-3 type composition) clad in silver was placed under the conductive coil. The entire probe was then placed in a Dewar vessel containing liquid nitrogen. The phase of a lock-in amplifier was set to minimize resistance and to maximize reactance. A current of about 1 milliampere RMS at about 1 Khz was passed through the conductive coil. A DC current source attached to the superconductive sample was gradually increased by steps of about 1 milliampere per second and voltage was collected. A plot of the measured inductive reactance versus applied current was generated and the plot is shown in FIG. 3. Critical current of the superconductive material was the point at which the inductive reactance deviated and was determined to be about 640 milliamperes.

EXAMPLE 2

Figure 4:
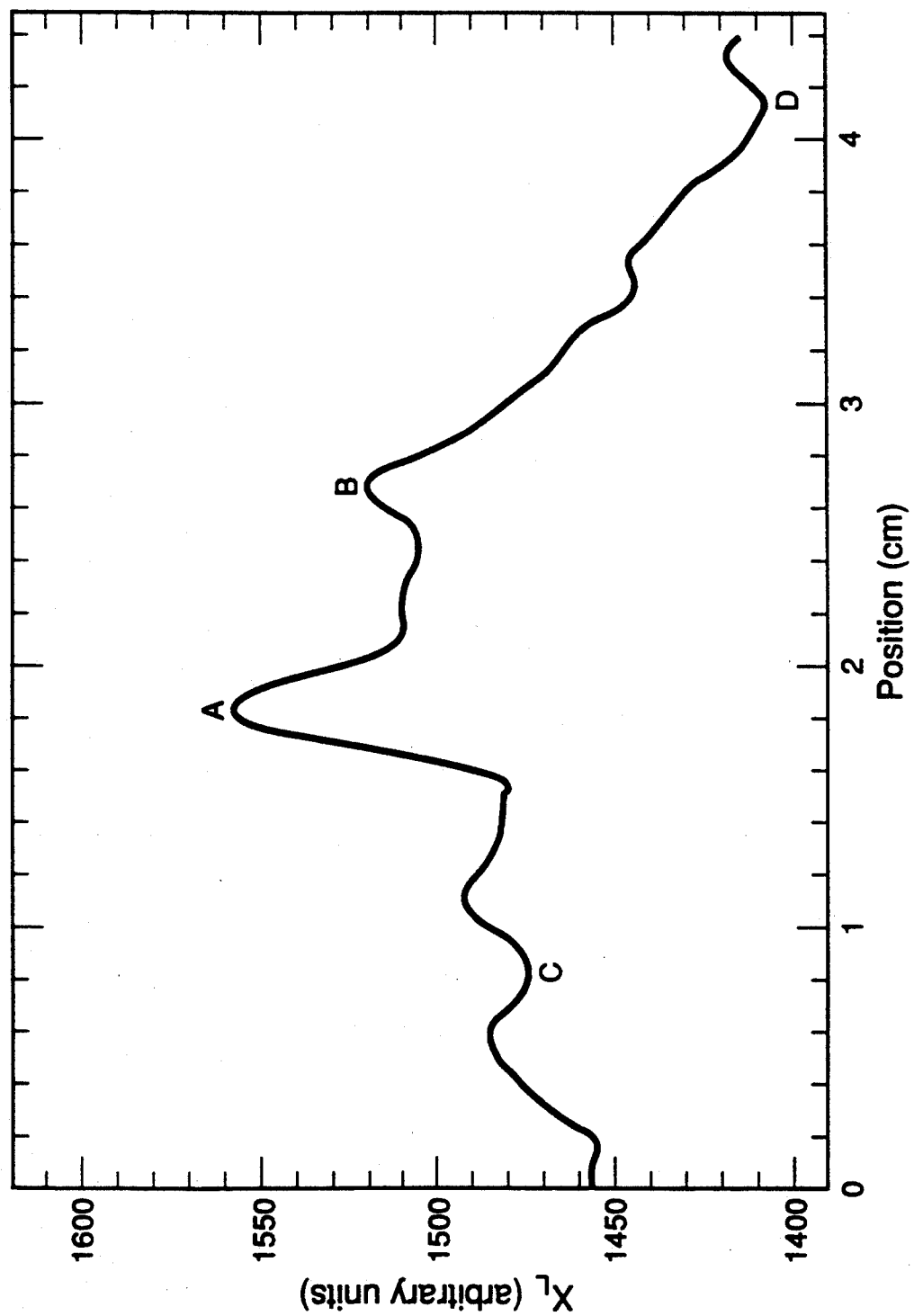
FIG. 4 shows a graph of measured relative inductive reactance ($X_L$) versus position of a superconductive wire in a run of the present process.
Figure 5:
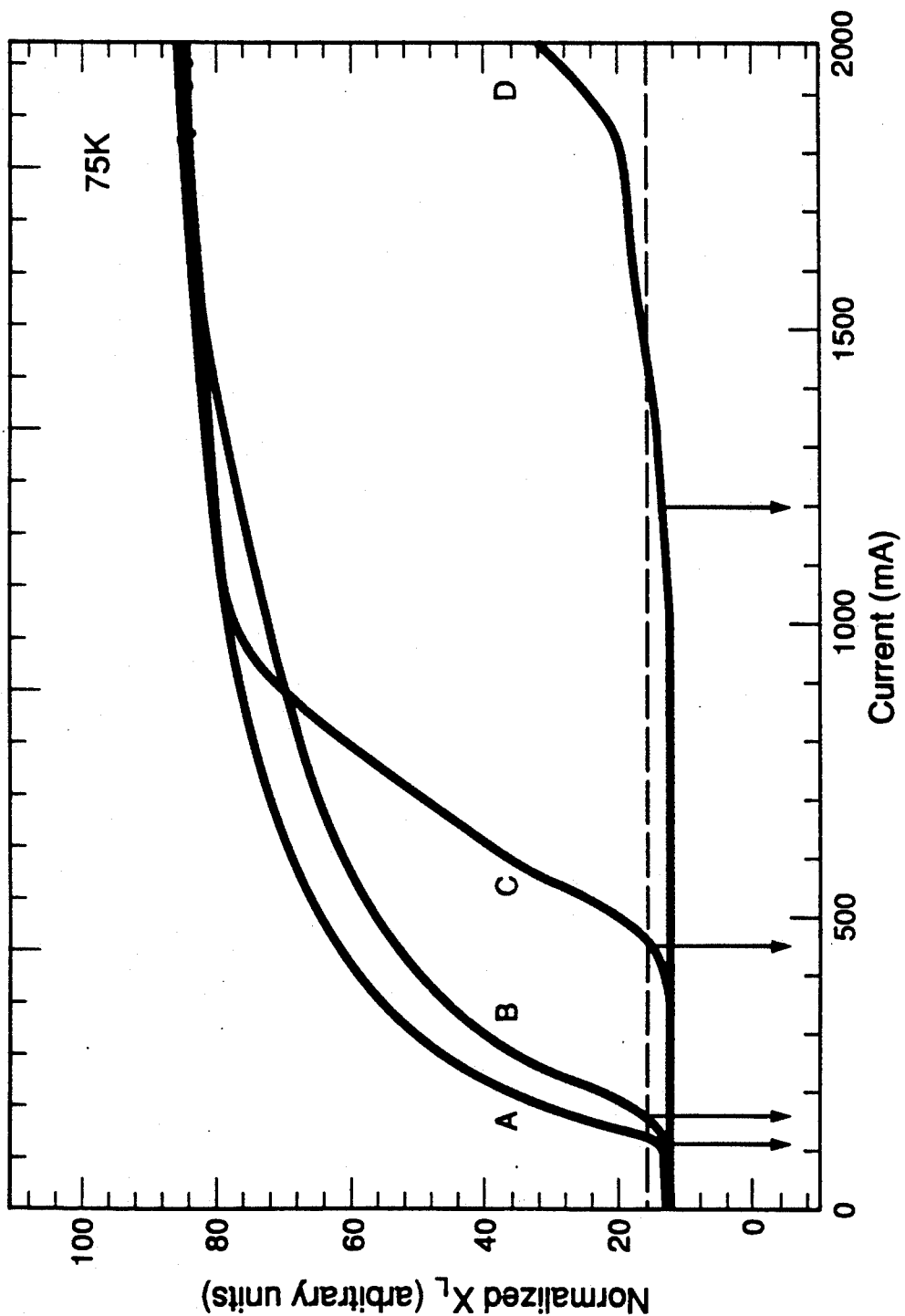
FIG. 5 shows a graph of measured normalized inductive reactance ($X_L$) at various points from FIG. 4 versus current supplied to the clad superconductive material in a run of the present process.

A conductive coil as in example 1 was mounted onto a probe as shown in FIG. 2 and a clad superconductive material of thallium-barium-calcium-copper oxide (a 2-2-2-3 type composition) clad in silver was placed under the conductive coil. The entire assembly was then placed in a Dewar vessel containing liquid nitrogen. A current of about 1 milliampere RMS at about 10 Khz was passed through the conductive coil. The fixture including the mounted clad superconductive material was moved gradually under the conductive coil and the relative inductive reactance or variations in inductive reactance was measured along the tape. A plot of the measured inductive reactance (arbitrary units) versus superconductive wire was generated and the plot is shown in FIG. 4. Essentially, it is variations in eddy currents that show in the scan. The result of this measurement indicates qualitative information about the underlying superconductive material, i.e., either the presence of varying amounts of superconductive material at a certain position or a variation in the quality of the superconductive material at a certain point. Further examination of the particular points of interest along the wire, shown as points A, B, C, and D in FIG. 4, were then conducted in a manner similar to the measurement in example 1. A plot of normalized inductive reactance (normalized so that each point begins at the same place on the y-axis) versus current for the measurements at points A, B, C, and D is shown in FIG. 5. Critical current of the superconductive material was the point at which the inductive reactance deviated for each measurement and was determined to be about 110 milliamperes at point A, about 160 milliamperes at point B, about 450 milliamperes at point C, and about 1200 milliamperes at point D.

Although the present invention has been described with reference to specific details, it is not intended that such details should be regarded as limitations upon the scope of the invention, except as and to the extent that they are included in the accompanying claims.

What is claimed is:

1. An apparatus for the measurement of the critical current of a superconductive sample comprising:
   a conductive coil;
   a means for maintaining the coil in proximity to a superconductive sample;
   an electrical connection means for passing a low amplitude alternating first current through the coil;
   a cooling means for maintaining the superconductive sample at a preselected temperature;
   a means for passing a second current through the superconductive sample; and,
   a means for monitoring reactance of the coil.

2. The apparatus of claim 1 wherein the superconductive sample is a clad superconductive material.

3. The apparatus of claim 2 wherein the means for passing the second current through the superconductive sample is an electrically connected direct-current source.

4. The apparatus of claim 3 wherein the means for monitoring reactance of the coil comprises a phase sensitive detector.

5. The apparatus of claim 4 wherein the phase sensitive detector is a lock-in amplifier.

6. The apparatus of claim 1 wherein the means for monitoring reactance of the coil comprises a phase sensitive detector.

7. The apparatus of claim 1 wherein the low amplitude alternating current passed through the coil is a low frequency current.

8. The apparatus of claim 1 wherein the means for passing the second current through the superconductive sample is an electrical connection means including a direct current source.

9. The apparatus of claim 1 further including a means for applying a magnetic field to the superconductive sample whereby critical currents can be measured as a function of applied magnetic field.

10. A process of measuring the critical current of a superconductive material comprising:
    placing a superconductive coil in the vicinity of a conductive coil, the coil included in an apparatus further including a coil mount, a means for passing a low amplitude alternating first current through the coil, a means for passing a second current through the superconductive material, and, a means for monitoring reactance of the coil;
    cooling the superconductive material to a preselected temperature;
    passing the low amplitude alternating first current through the coil, the alternating current capable of generating a magnetic field sufficient to penetrate and to induce eddy currents in the superconductive material;
    passing a steadily increasing second current through the superconductive material, the second current characterized as having a different frequency than the alternating first current; and,
    monitoring the reactance of the coil with a phase sensitive detector as the second current is steadily increased whereby the critical current of the superconductive material can be observed as the point whereat a component of impedance deviates.

11. The process of claim 10 wherein the superconductive material is a clad superconductive material.

12. The process of claim 11 wherein the second current passing though the superconductive material is a direct current.

13. The process of claim 12 wherein the low amplitude alternating first current passing through the coil is a low frequency current.

14. The process of claim 13 wherein the phase sensitive detector is a lock-in amplifier.

15. The process of claim 10 wherein the second current passing through the superconductive material is a direct current.

16. The process of claim 10 wherein the low amplitude alternating first current passing through the coil is a low frequency current.

17. The process of claim 10 wherein the phase sensitive detector is a lock-in amplifier.

18. The process of claim 10 further including applying a magnetic field to the superconductive sample whereby critical current can be measured as a function of applied magnetic field.

* * * * *